US009655763B2

(12) United States Patent
Bruckmann

(10) Patent No.: US 9,655,763 B2
(45) Date of Patent: *May 23, 2017

(54) MOBILIZING MUSCULOSKELETAL STRUCTURES

(71) Applicant: J. W. Barry Bruckmann, Nassau (BS)

(72) Inventor: J. W. Barry Bruckmann, Nassau (BS)

(*) Notice: Subject to any disclaimer, the term of this patent is extended or adjusted under 35 U.S.C. 154(b) by 426 days.

This patent is subject to a terminal disclaimer.

(21) Appl. No.: 14/489,976

(22) Filed: Sep. 18, 2014

(65) Prior Publication Data

US 2015/0025434 A1 Jan. 22, 2015

Related U.S. Application Data

(63) Continuation of application No. 12/436,696, filed on May 6, 2009, now Pat. No. 8,864,698.

(60) Provisional application No. 61/050,928, filed on May 6, 2008.

(51) Int. Cl.
| | | |
|---|---|---|
| *A61F 5/00* | (2006.01) | |
| *A61F 13/00* | (2006.01) | |
| *A41D 13/08* | (2006.01) | |
| *A61F 5/058* | (2006.01) | |
| *A43B 5/00* | (2006.01) | |
| *A43B 7/00* | (2006.01) | |
| *A61F 5/01* | (2006.01) | |
| *A61F 5/10* | (2006.01) | |

(52) U.S. Cl.
CPC ............ *A61F 5/05875* (2013.01); *A43B 5/00* (2013.01); *A43B 7/00* (2013.01); *A61F 5/019* (2013.01); *A61F 5/0118* (2013.01); *A61F 5/0195* (2013.01); *A61F 5/10* (2013.01)

(58) Field of Classification Search
CPC ................................................... A61F 5/05875
USPC ............ 602/1, 5, 23, 30, 22, 21; 36/44, 159, 36/178, 181, 145, 166; 2/160, 21, 16, 2/455; 128/878, 879, 880, 898, 888–889
See application file for complete search history.

(56) References Cited

U.S. PATENT DOCUMENTS

| | | | |
|---|---|---|---|
| 1,337,879 | A | 4/1920 | Bean |
| 2,237,251 | A | 4/1941 | Longfellow |
| 2,354,770 | A | 8/1944 | Jane |
| 2,633,129 | A | 3/1953 | Crawford |
| 3,211,142 | A | 10/1965 | Johannes |
| 4,084,586 | A | 4/1978 | Hettick |
| 4,103,682 | A | 8/1978 | Franzl |

(Continued)

FOREIGN PATENT DOCUMENTS

| | | |
|---|---|---|
| GB | 2437925 A | 11/2007 |
| GB | 2457779 A | 9/2009 |

(Continued)

OTHER PUBLICATIONS

Boyd et al., "Principles of Casting and Splinting", American Family Physician. vol. 79, No. 1, Jan. 1, 2009, 16-22.

(Continued)

*Primary Examiner* — Tarla Patel
(74) *Attorney, Agent, or Firm* — Edna Vassilovski

(57) ABSTRACT

An injured musculoskeletal structure is mobilized relative to a juxtaposing support structure surface to isolate the injured musculoskeletal structure from forces transferred from adjoining musculoskeletal structures in order to alleviate pain, discomfort, inflammation, and further injury associated with such transferred forces.

21 Claims, 11 Drawing Sheets

(56) References Cited

U.S. PATENT DOCUMENTS

| | | | |
|---|---|---|---|
| 4,571,960 | A | 2/1986 | Hursh |
| 4,631,841 | A | 12/1986 | Hickey |
| 4,644,941 | A | 2/1987 | Ogle |
| 4,765,320 | A | 8/1988 | Lindemann |
| 4,781,178 | A | 11/1988 | Gordon |
| 4,899,737 | A | 2/1990 | Lazarian |
| 4,959,059 | A | 9/1990 | Eilender |
| 5,151,081 | A | 9/1992 | Williams |
| 5,154,692 | A | 10/1992 | Lockhart |
| 5,474,525 | A | 12/1995 | Blott |
| 5,499,966 | A | 3/1996 | Bulley |
| 5,586,398 | A | 12/1996 | Carlson |
| 5,590,420 | A | 1/1997 | Gunn |
| 5,769,805 | A | 6/1998 | Lockhart |
| 5,823,981 | A | 10/1998 | Grim |
| 5,925,008 | A | 7/1999 | Douglas |
| 5,933,984 | A | 8/1999 | Carlson |
| 5,957,875 | A | 9/1999 | Lockhart |
| 6,083,185 | A | 7/2000 | Lamont |
| 6,102,878 | A | 8/2000 | Nguyen |
| 6,261,253 | B1* | 7/2001 | Katzin ................ A61F 5/0118 602/12 |
| 6,362,387 | B1 | 3/2002 | Carlson |
| 6,478,761 | B2 | 11/2002 | Bracamonte |
| 6,575,925 | B1 | 6/2003 | Noble |
| 6,592,584 | B2 | 7/2003 | Agee |
| 6,592,589 | B2 | 7/2003 | Hajianpour |
| 6,866,043 | B1 | 3/2005 | Davis |
| 6,932,682 | B2 | 8/2005 | Kostar |
| 6,932,782 | B2 | 8/2005 | Ferraioli |
| 6,953,441 | B2 | 10/2005 | Goumas |
| 6,964,645 | B1 | 11/2005 | Smits |
| 7,169,121 | B2 | 1/2007 | Berrehail |
| 7,266,910 | B2 | 9/2007 | Ingimundarson |
| 7,574,748 | B2* | 8/2009 | Fisher .............. A41D 19/01588 2/16 |
| 2004/0019308 | A1 | 1/2004 | Chow |
| 2004/0225246 | A1 | 11/2004 | Doctor |
| 2005/0101898 | A1 | 5/2005 | Cohen |
| 2005/0234375 | A1 | 10/2005 | Grim |
| 2006/0135899 | A1 | 6/2006 | Jerome |
| 2006/0155233 | A1* | 7/2006 | Huber ................ A61F 5/0102 602/30 |
| 2011/0245747 | A1 | 10/2011 | Wollstein |

FOREIGN PATENT DOCUMENTS

| | | |
|---|---|---|
| WO | WO9811850 A1 | 3/1998 |
| WO | WO2006104920 A3 | 4/2007 |
| WO | WO2006084220 A3 | 6/2007 |
| WO | WO2008051168 A1 | 5/2008 |

OTHER PUBLICATIONS

Broken Finger, WebMD, http://www.webmd.com/a-to-z-guides/broken-finger, Jun. 17, 2009, 2 pages.

Broken toe information at MyFootShop, http://www.myfootshop.com/detail.asp?Condition=Broken%20Toe, Jun. 17, 2009, 3 pages.

Broken toe: How is it treated?—MayoClinic.com, http://www.mayclinic.com/health/broken-toe/AN01719/METHOD=print, Jun. 17, 2009, 2 pages.

Cluett, J, "Finger Injuries—Finger Fractures", http://www.orthopedics.about.com/cs/generainfor3/a/fingerinjury, Jun. 17, 2009, 2 pages.

Foot Anatomy, eOrthopod, http://www.eorthopod.com/public/patient_education/6479/foot_anatomy.html, Jun. 17, 2009, 5 pages.

Foot Care Products, MyFootShop, http:www.myfootshop.com/SearchResults_simple.asp?Method=Category&Value=Foot% . . . , Jun. 17, 2009, 2 pages.

Hatch et al., "Evaluation and Management of Toe Fractures", American Family Physician. vol. 68, No. 12, Dec. 15, 2003, 2413-2418.

Thumb Spica Splints, http://www.braceshop.com/productcart/pc/THUMB-SPICA-SPLINTS-c61.htm Jun. 17, 2009, 3 pages.

Your Orthopaedic Connection: Toe and Forefoot Fractures, http://orthoinfo.aaos.org/topic.cfm?topic=A00165, Jun. 17, 2009, 2 pages.

EPO Examination Report for Application No. 09742467.5-2310 dated Dec. 30, 2011, 4 pages.

Notification of Transmittal of the International Search Report and Written Opinion in International Application No. PCT/IB2009/005901 dated Nov. 17, 2009, 15 pages.

European Patent Office Action for Application No. 13162086.6-1654 dated Jun. 7, 2013, 5 pages.

Invitation to Pay Additional fee and, where applicable, Protest Fee, Including Results of the Partial International Search, issued in PCT/US2014-029870 on Jul. 2, 2014, 5 pages.

U.S. Non-Final Office Action for U.S. Appl. No. 12/436,696 dated May 26, 2011, 16 pages.

U.S. Final Office Action for U.S. Appl. No. 12/436,696 dated Feb. 1, 2012, 15 pages.

Notice of Allowance issued in U.S. Appl. No. 12/436,696 on Jul. 3, 2014, 24 pages.

* cited by examiner

MOBILIZING MUSCULOSKELETAL STRUCTURES

RELATED APPLICATION

This application is a continuation of U.S. application Ser. No. 12/436,696, filed on May 6, 2009, which claims the benefit of U.S. Provisional Application No. 61/050,928, filed on May 6, 2008, the contents of which are incorporated by reference.

TECHNICAL FIELD

This disclosure relates to mobilizing musculoskeletal structures, including injured musculoskeletal structures.

BACKGROUND

Casts, splints, bandages, and braces are used to stabilize, immobilize, or otherwise protect or support, musculoskeletal disorders such as traumatic injuries, e.g., fractures, deformities, and other problems of bones, joints, and connective tissues of the body ("injury sites"). Protecting and supporting the injury site can assist in reducing pain or discomfort, reducing inflammation, providing physical support, promoting healing, and protecting from further damage or injury. Supporting and protecting an injury site typically involves immobilizing the injury site. For example, one treatment for fractures of the bones of the toes (the phalanges) includes taping the injured toe to an adjacent toe to limit independent movement of the injured toe. Additionally or alternatively, a splint is sometimes attached to an injured toe in an attempt to immobilize and protect the injured toe.

SUMMARY

An injured musculoskeletal structure, such as a broken toe or finger bone, is also susceptible to painful and potentially damaging forces. Particularly, normal use of interconnected musculoskeletal structures can transfer forces to the injury site, potentially causing pain and inflammation, and potentially hindering healing of the injury. For example, when a person steps down on the foot, the metatarsals normally move down and forward in relation to the heel, and they also spread to the sides in relation to one another. Thus, mobilizing an injured musculoskeletal structure relative to a support device can allow natural movement of the injured musculoskeletal structure, and can reduce undesired transfer of forces to the injured musculoskeletal structure during healing.

In one general aspect, a device includes a shell member sized and shaped to juxtapose an injured digit of a limb during healing. The shell member has a digit-facing surface formed of a slippery material to mobilize the injured digit relative to the shell member. The device also includes means for limiting movement of the shell member relative to an adjacent healthy musculoskeletal structure of the limb.

Some implementations may include one or more of the following features. The device includes an interface member disposed between the injured digit and the shell member to facilitate movement of the injured digit relative to the shell member. The means for limiting movement of the shell member relative to an adjacent healthy musculoskeletal structure includes a slip-resistant body-facing surface juxtaposing the adjacent healthy musculoskeletal structure of the limb. The means for limiting movement of the shell member relative to an adjacent healthy musculoskeletal structure includes a hook-and-loop fastener.

The shell member is formed as a shoe insole. The device includes an upstanding deflection member configured to at least partially cover an injured toe. The digit-facing surface includes an upper surface portion of the shell member on which a wearer's foot rests during use, and the means for limiting movement includes an upper surface portion of the shell member on which the wearer's heel or instep rests during use. The shell member defines a space in which the wearer's heel does not rest on the shell during use, and the means for limiting movement of the shell member relative to an adjacent healthy musculoskeletal structure of the limb includes the space.

The device includes an interface member formed as a sock configured to cover a wearer's foot, and the sock is configured for sliding engagement with the digit-facing surface and substantially non-sliding engagement with the upper surface portion of the shell member on which the wearer's heel or instep rests.

The shell member defines an interior cavity configured to receive at least a portion of the injured digit, and the digit-facing surface includes an inner surface of the shell member. The device further includes an interface member including a splint or a sleeve. The device includes a deflection member configured to at least partially enclose the injured digit to protect the injured digit from damaging contact.

The device includes a shoe member that is configured to receive the shell member. The shoe member includes the means for limiting movement of the shell member relative to an adjacent healthy musculoskeletal structure of the limb.

In another general aspect, a splint for supporting an injured musculoskeletal structure includes a rigid supportive shell configured to cradle an injured musculoskeletal structure. The supportive shell limits bending of the injured musculoskeletal structure in a first direction. An interface member is disposed between a portion of a wearer's body and at least a portion of the supportive shell to mobilize at least one of the injured musculoskeletal structure and a musculoskeletal structure adjacent to the injured musculoskeletal structure relative to the supportive shell.

In another general aspect, a process includes providing a device for mobilizing an injured musculoskeletal structure to slide relative to an orthotic member juxtaposing the injured musculoskeletal structure to support the injured musculoskeletal structure during healing.

In another general aspect, supporting an injured musculoskeletal structure during healing includes mobilizing the injured musculoskeletal structure to slide relative to an orthotic member juxtaposing the injured musculoskeletal structure.

Some implementations may include one or more of the following features. Supporting an injured musculoskeletal structure includes isolating the injured musculoskeletal structure from the orthotic member such that the orthotic member limits the transfer of a force to the injured musculoskeletal structure when moving with a body portion to which the orthotic member is attached. The method includes retaining the orthotic member to a healthy musculoskeletal structure during use, substantially limiting bending of the injured musculoskeletal structure in a first direction, or at least partially enclosing the injured musculoskeletal structure to protect against damaging contact.

In another general aspect, supporting an injured musculoskeletal structure includes placing an interface member on an exterior skin surface juxtaposing the injured musculoskeletal structure and placing a shell member in a position juxtaposing the injured musculoskeletal structure. The interface member facilitates sliding movement of the injured musculoskeletal structure and/or an adjacent musculoskeletal structure relative to the shell member during support.

In another general aspect, a device includes a shell member sized and shaped to juxtapose an injured toe during healing. The shell member includes a first, foot-facing surface portion formed of a slippery material to mobilize the injured toe relative to the first surface portion, and a second, foot-facing surface portion having a higher coefficient of friction than the first surface portion and arranged relative to the first surface portion to support a healthy musculoskeletal structure adjacent the injured toe and to limit sliding between the second surface and the healthy musculoskeletal structure.

In another general aspect, a device includes a shell member sized and shaped to juxtapose a foot sole at a location proximate an injured toe while not juxtaposing adjacent portions of the sole. The shell member includes a foot-facing surface formed of a slippery material to mobilize the injured toe relative to the foot-facing surface.

In another general aspect, a device includes a shell member sized and shaped to juxtapose an injured finger or thumb during healing. The shell member includes a first digit-facing surface portion formed from a slippery material to mobilize the injured finger or thumb relative to the first surface portion and a second surface portion configured to immobilize the shell member relative to healthy musculoskeletal structure adjacent the injured finger or thumb.

In another general aspect, a device includes a shell member sized and shaped to juxtapose an injured metacarpal structure during healing. The shell member includes a first surface portion configured to immobilize the shell member relative to the injured metacarpal structure and a second digit-facing surface portion formed from a slippery material to mobilize a finger or thumb adjacent the injured metacarpal structure relative to the second surface portion.

In one general aspect, a device includes a shell member sized and shaped to juxtapose an injured musculoskeletal structure of a limb during healing. The shell member has a surface configured to face the injured musculoskeletal structure and/or an adjacent musculoskeletal structure. The surface is formed of a slippery material to mobilize the injured musculoskeletal structure and/or the adjacent musculoskeletal structure relative to the shell member. The device also includes means for limiting movement of the shell member relative to an adjacent healthy musculoskeletal structure of the limb.

In some implementations, musculoskeletal structures adjacent to an injured musculoskeletal structure are mobilized. For example, other bones, skeletal muscles, cartilage, and/or tendons in the forefoot, in addition to the injured musculoskeletal structure, can be mobilized relative to a support device to limit painful and/or injurious forces from being transferred to an injured toe during standing or walking. In other implementations, the musculoskeletal structures adjacent to, and/or adjoining an injured musculoskeletal structure are mobilized instead of the injured musculoskeletal structure. Additionally, the mobilized adjacent and/or adjoining musculoskeletal structures include those structures distal to the injured musculoskeletal structure. For example, a healthy toe can be mobilized relative to a support device to protect a connected metatarsal bone or joint such that when the metatarsal bone pushes forward or outward against the toe during walking, the mobilized toe moves with the internal motion of the connected metatarsal bone. Mobilizing the toe minimizes resistance against such internal movements of the metatarsal bone, and reducing painful and/or injurious forces transferred to the injury site.

The details of various implementations set forth in the accompanying drawings and description. Other features and advantages will be apparent from the description and drawings, and from the claims.

BRIEF DESCRIPTION OF THE DRAWINGS

Like reference symbols in the various drawings indicate like elements.

DETAILED DESCRIPTION

An injured musculoskeletal structure is mobilized relative to a juxtaposing support device by a low friction interface provided where the support device contacts the injury site. For example, as will be discussed in further detail below, in the case of a toe fracture the support device provides a slippery surface located on a surface facing the injured toe such that a very low friction interface is provided between the injured toe and the support device. This allows the injured toe to move relative to the support device when pressure is applied to the foot, e.g., when the patient stands or walks, causing the metatarsal bones to spread and push forward in relation to the heel of the foot and in relation to the support device. Because the toe can slide over the slippery surface to accommodate these movements of the musculoskeletal structure of the foot, pressure and stress on the toe are reduced, thereby reducing pain and inflammation, and reducing the likelihood of further damage to the injured toe.

Figure 1:
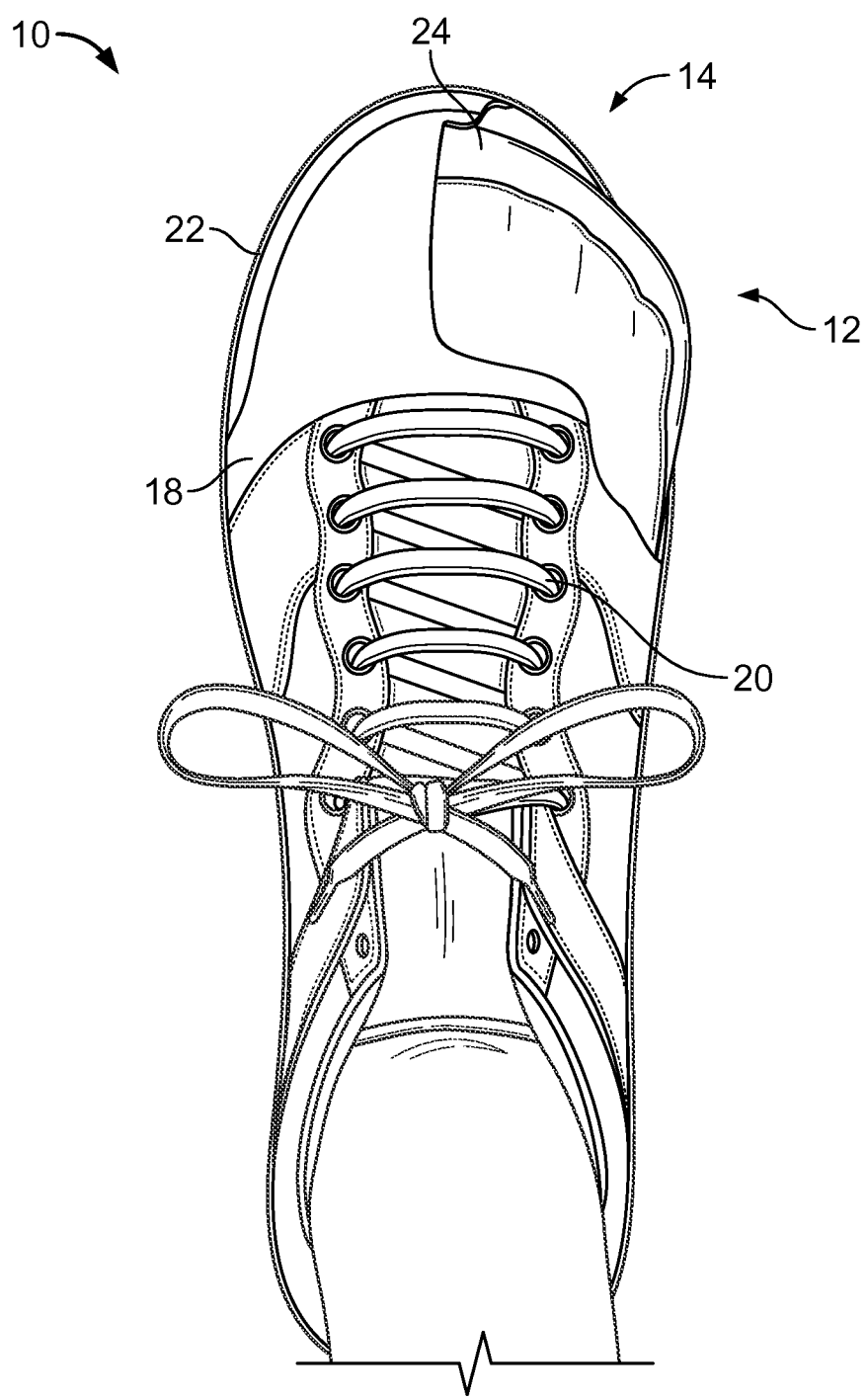
FIG. 1 is a top view of an orthotic support device according to one implementation.
Figures 2, 2A:
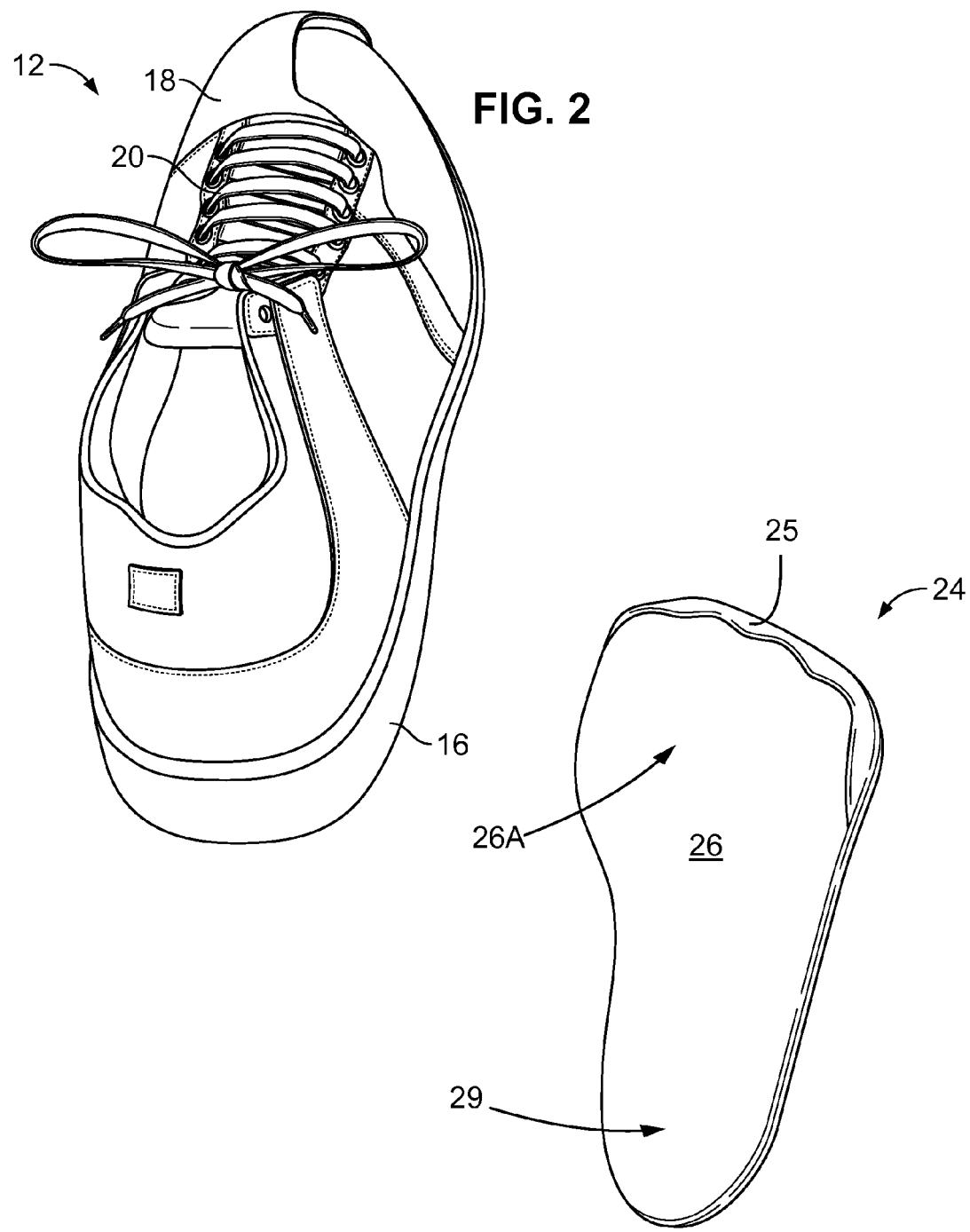
FIG. 2 is a perspective view of the orthotic support device shown in FIG. 1, with the low friction liner removed.
FIG. 2A is a plan view of the low friction liner of the orthotic support device shown in FIG. 1.
Figure 3:
FIG. 3 is a side view of the orthotic support device shown in FIG. 1 with the low friction liner removed.

Referring to FIGS. 1-3, a mobilizing support device 10 for supporting an injured foot, e.g., having a toe fracture, a deformed toe, or other musculoskeletal injury, includes a shoe portion 12 having an open area 14 surrounding the injury site. The open area 14 is arranged such that contact between the injured musculoskeletal structure of the foot and the shoe portion 12 is reduced or eliminated. Thus, during walking or standing, the shoe portion 12 does not contact the top, end, or sides of the injured musculoskeletal structure. The shoe portion 12 includes a sole 16, an upper 18, a lacing system 20, and a toe cover 22 positioned adjacent the open area 14 to protect uninjured toes from impact with external objects.

Figure 5:
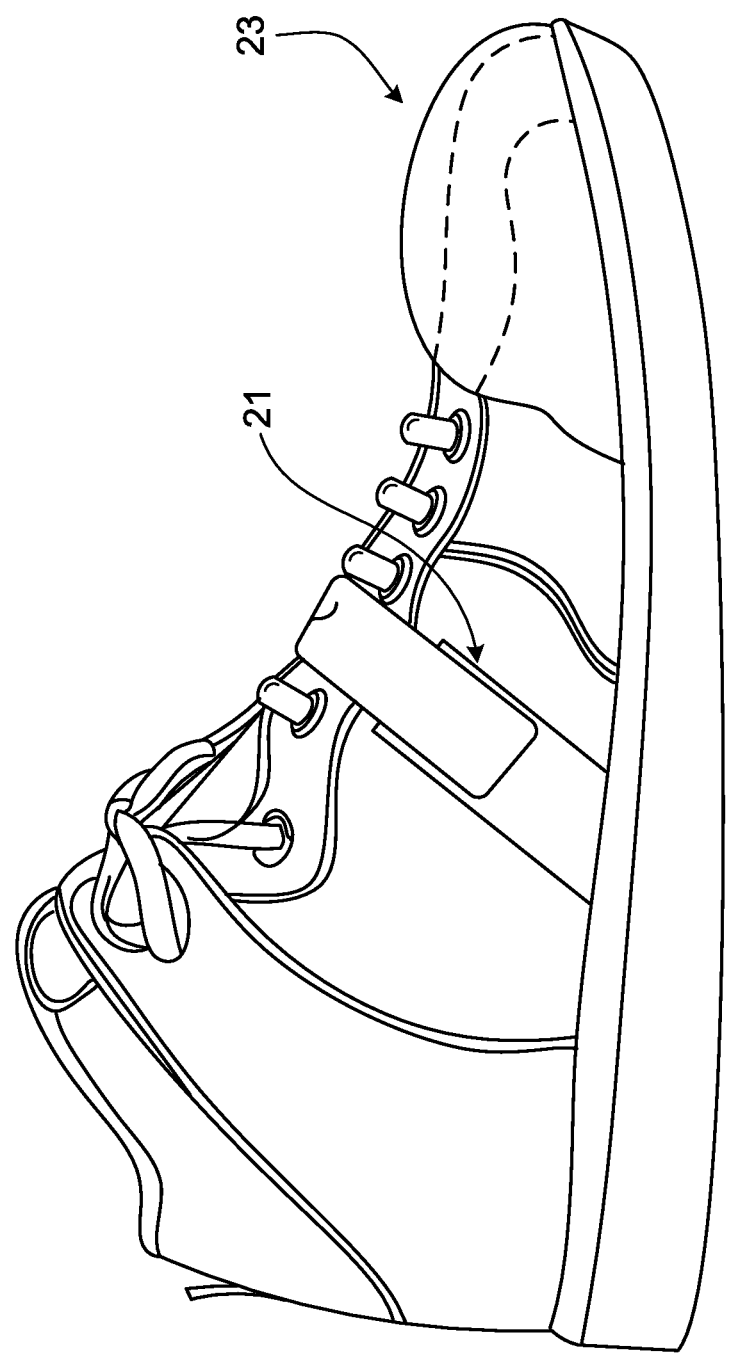
FIG. 5 is a side view of an orthotic support device in which an open area of the shoe portion of the device is replaced by an enlarged protective area.

In an alternative embodiment, shown in FIG. 5, the open area 14 and toe cover 22 are replaced, at least in part, by an enlarged, protective area 23. Protective area 23 has sufficient dimensions to provide clearance around the injured musculoskeletal structure. For example, the protective area 23 provides a clearance distance of from about 0.125" to about 1.0" around the top, end, and sides of the injured toe(s), and is formed of a material that is sufficiently stiff to provide a desired degree of protection to the toes from an impact from the front or above, e.g., an object being dropped on the foot. The protective area 23 can include perforations or other ventilation structure, and can be lined with a low friction material to provide a low friction sliding interface with the toes in case the toes contact the inner surface of the enlarged protective area 23. Ideally, the open area or enlarged area is configured to allow the injury site to slide relative to the insole, as will be discussed further below, without contact of the upper part of the injured area with the device 10.

The lacing system 20 holds in place a portion of the limb that is adjacent to the injury site, such as the heel, ankle, and/or calf, relative to the shoe portion 12 and allows adjustment of the size of the shoe, e.g., to accommodate swelling and to allow the wearer to easily don and remove the shoe. For example, the lacing system can retain musculoskeletal structures of the heel and/or ankle in generally slip-free communication with the upper 18. The lacing system can be replaced by, and/or supplemented with, any suitable attachment device, for example hook and loop fastener strips such as those available commercially under the tradename Velcro®, or other adjustable straps. Snaps, clips, buckles, and other latching and/or cinching devices can also be used. In some implementations, the upper 18 extends over the ankle area, to provide additional support and immobilization of selected musculoskeletal structures of the foot relative to the shoe portion 12. For example, the upper 18 may be similar to that of a high top sneaker, a hiking shoe, or boot.

Referring to FIG. 2, a liner 24 is disposed inside the shoe 12, and functions both as an insole and as a low-friction sliding surface. As shown in FIG. 1, the liner 24 is sized such that it extends beyond the position of the toes when weight is carried by the foot, so that there is room for the toes to slide forward and outward when the wearer steps or stands on the foot. For example, the liner 24 extends horizontally a distance of approximately 0.25" or more beyond the perimeter of expected movements of the forefoot when walking or standing, in order to ensure adequate space for unimpeded movement of the toes and to provide protection from side impacts. In some embodiments, this side protection can be enhanced by including an upstanding protective portion 25 that extends upward slightly and curves, forming a cavity to partially enclose one or more toes.

Figure 4:
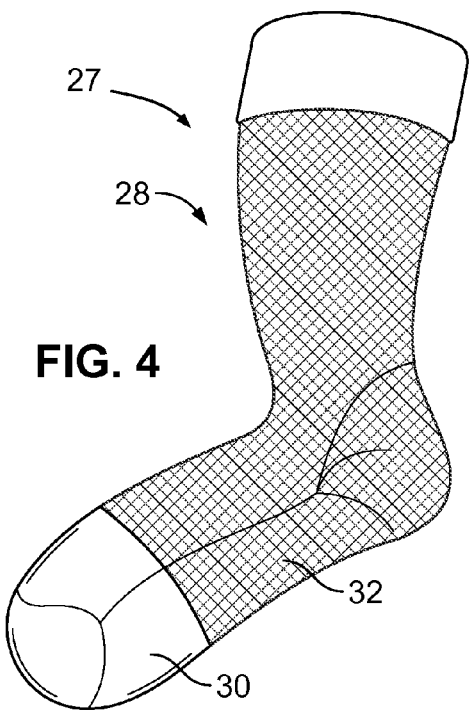
FIGS. 4 and 4A are diagrammatic views of socks according to two implementations.
Figure 6:
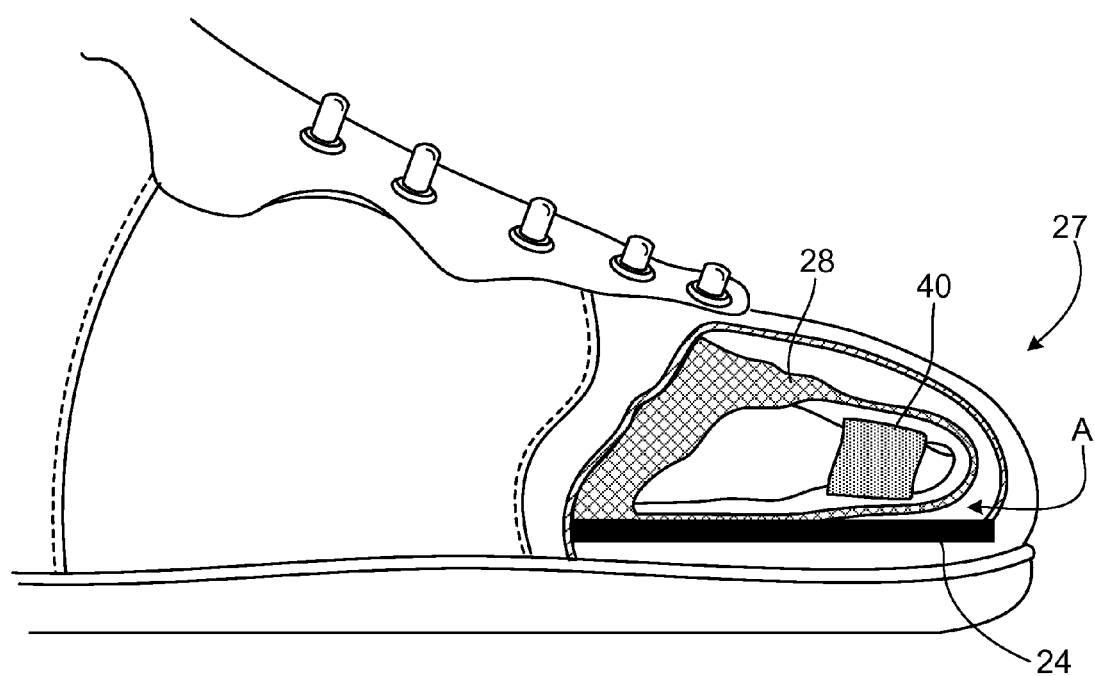
FIG. 6 is a partial cut-away side view of the orthotic support device of FIG. 1 in use with a toe splint.

In use, and as shown in FIG. 6, the liner 24 is disposed juxtaposing an injured musculoskeletal structure and healthy musculoskeletal structures adjacent to the injured musculoskeletal structure. The liner 24 includes a slippery surface 26 that provides an interface having a low coefficient of friction and can be formed of any material that, with the shoe, provides the necessary support for the particular application. The support device 10 additionally includes an interface member 27 that covers at least a portion of the wearer's skin to cooperate with the slippery surface 26. As illustrated in FIG. 4, the interface member 27 can be a sock 28 to cover a foot having an injured musculoskeletal structure. Depending on the material of the interface member 27, suitable materials for the slippery surface 26 can include polytetrafluoroethylene, polyethylene, polypropylene, nylon, or the like. In some cases, the liner 24 may be formed of a heat moldable material, to allow the liner to be shaped to portions of the wearer's foot if desired. For example, the liner can be molded to serve as a supportive footbed, providing arch support and/or other ergonomic or therapeutic support to the foot while walking, in addition to providing a slippery surface for mobilization of injured musculoskeletal structures and/or adjacent musculoskeletal structures. One suitable material for use as the liner 24 is commercially available from Sammons Preston (www.sammonspreston.com) under the tradename Aquaplast®.

The stiffness or flexibility of all, or parts of, the support device 10 can be achieved by varying the flexibility of the shoe portion 12 and/or of the liner 24, and can be varied as may be required for treating different conditions. The support device can be or can include portions that are rigid, semi-rigid, or flexible, as appropriate for a given implementation. In most cases, it will be desirable for the support device 10 to be rigid enough to minimize bending motion around the injury site. In some cases, the support device 10 can be supplied to a healthcare provider, or to the end user, with a set of liners 24 having different thicknesses, or other characteristics, to allow the shoe portion 12 to be easily adapted to treat a variety of different injuries or conditions. Similarly, the healthcare provider can be supplied with a plurality of shoe portions 12 having different sizes and/or performance characteristics, to allow the healthcare provider to select a shoe portion 12 to meet a particular patient's needs.

If desired, the liner 24 can include multiple layers, e.g., an upper layer to provide the slippery surface 26 and a lower layer to provide other properties such as cushioning or shock absorption. In such cases one of the layers, e.g., the upper layer, can provide the desired level of stiffness and support. Alternatively, the shoe portion 12 may include a layer of foam or other cushioning material disposed under the liner 24, for example the sole 16 can provide cushioning.

As discussed above, interface member 27 can be formed as a sock 28 of conventional design, and should generally have elastic properties that allow the sock 28 to expand and contract along with the skin of the foot with minimal restriction of the natural expansion or contraction of the foot during standing or walking. In the area A of the injury site (FIG. 6) where unrestrained sliding movement is desired, the fabric of the sock 28 should slide freely and readily on the liner 24, with the interface therebetween having a low coefficient of friction to mobilize the injured toe. Additionally, musculoskeletal structures surrounding the injured toe, such as healthy musculoskeletal structures of the forefoot, including metatarsal structures, are mobilized. Preferably, the sock 28 includes materials or fibers that allow the foot to breathe and allow perspiration to be vented for general health as well as to minimize the possibility of moisture altering the coefficient of friction at the slippery surface 26. Other physical properties, e.g.; elasticity or padding, of one or more areas of the sock 28, or of any interface member 27, can be varied as may be appropriate for differing health conditions.

In some implementations, the liner 24 has one or more slippery areas 26A having a relatively low coefficient of friction, which are disposed juxtaposing the injury site(s), and one or more non-slip areas 29 having a relatively higher coefficient of friction, which are disposed away from the injury site, juxtaposing musculoskeletal structures of the foot that are adjacent to the injury site. For example, the liner can be sized and shaped to juxtapose substantially the entire bottom surface of the wearer's foot. An area 29 of the liner 24 that juxtaposes the wearer's heel has a relatively high coefficient of friction to limit the foot sliding forward in the shoe for limiting movement of the liner 24 relative to the heel or other adjacent healthy musculoskeletal structure of the limb. The area 26A of the liner 24 that juxtaposes the toes is slippery and has a relatively low coefficient of friction to allow the toes to move as the foot spreads. In some implementations, the liner 24 can be formed by comolding two different polymeric compositions. Additionally, a separate insole portion can be disposed on the liner to limit sliding of the foot. In other implementations, the liner 24 is sized and shaped such that it does not juxtapose the heel and/or instep of the wearer's foot during use, and sliding between the wearer's heel and/or instep can be limited by the shoe portion 12, as discussed above.

Referring to FIG. 4, a sock 28 has a first region 30 juxtaposing the injury site having a low coefficient of friction, e.g., formed of a synthetic fiber or a combination of fibers or yarns, such as nylon and rayon, such as to provide a low friction interface with the slippery surface 26. A second region 32, e.g., in the heel area, has a relatively higher coefficient of friction. The second region 32 may be formed using a rougher texture knit, and/or using fibers or yarns having a higher coefficient of friction. This sock construction allows the toes to slide freely relative to the liner 24 as the foot spreads, while helping to keep the rest of the foot in place within the shoe.

Figure 4A:
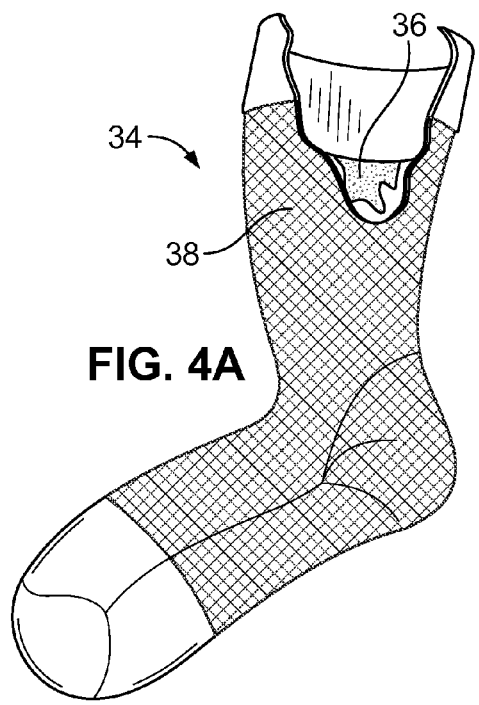

Referring to FIG. 4A, a sock 34 may have two or more layers, to provide desired comfort characteristics. For example, in the embodiment shown the sock includes an inner, moisture wicking layer 36, e.g., of cotton, a cotton blend, or a hydrophilic synthetic material. Also, in some implementations, the sock 28 or the sock 34 can be constructed of the same material, or combination of materials, throughout. In such embodiments, the variations of coefficient of friction are accomplished by variation of portions of the chosen interfacing surfaces.

Now referring to FIG. 6, the interface member 27 can include, integrally or in combination, a splint 40, or other device configured to support an injured musculoskeletal structure, such as a broken phalange of a toe. The splint 40 can be used for localized support, such as to support a joint or to maintain desired alignment of bone portions of the fracture bone, and can be used with or without a fabric covering the splint 40, such as the sock 28. While the splint 40 can be considered an immobilizing device, the slippery surface 26 of the liner 24 still allows the splint 40 to slide freely thereover during standing or walking. Additionally, even when the splint 40 is used, phalanges or metacarpals, can be mobilized relative to the slippery surface 26 of the liner 24. The slippery surface 26 can be selected from a material that creates a low friction interface with an external surface of the splint 40, including tape or the like that may be used to attach the splint 40 to the injured musculoskeletal structure. This splint can be rigid, semi-rigid or flexible, and can be formed from any combination of fabrics, foams, suitable metals and/or plastics, such as elastic sleeves, elastic or inelastic bandaging, or conventional splints for digits. To provide sliding interaction, the slippery surface 26 can be formed from polytetrafluoroethylene, polypropylene, or polyethylene, among other materials.

Figure 7:
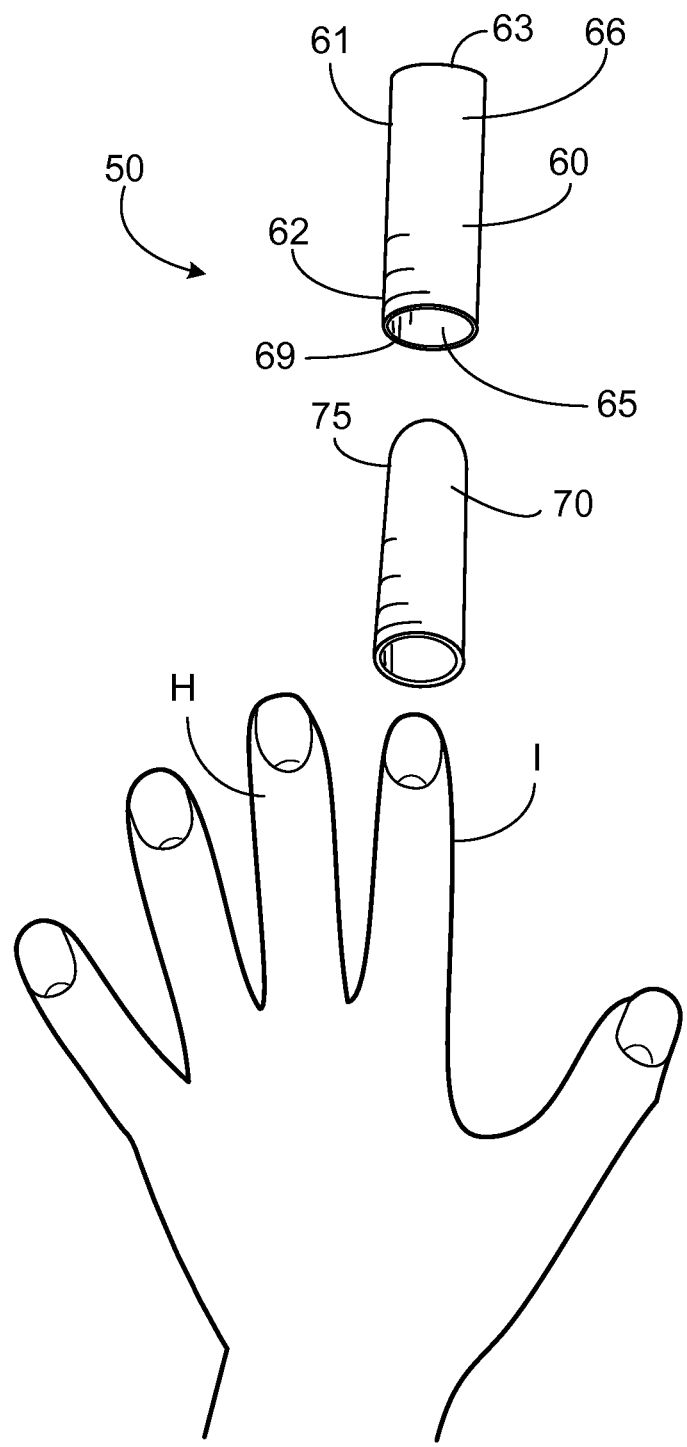
FIG. 7 is an exploded view of another orthotic support device.
Figure 8:
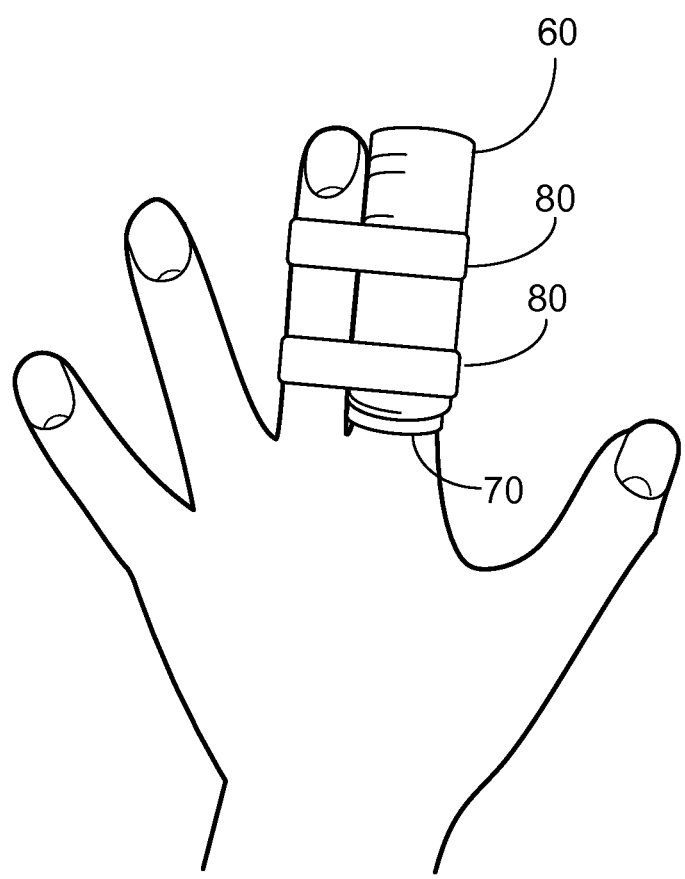
FIG. 8 is a perspective view of the orthotic support device of FIG. 7 in use.

While the support device 10 of FIGS. 1-6 is suitable for mobilizing support of an injured musculoskeletal structure in the foot, including toes and joints, other support devices can be used to mobilize injured musculoskeletal structures of the foot, or of other parts of the body. Referring to FIG. 7, a mobilizing support device 50 includes a rigid digit-receiving support shell 60 and a digit-covering interface member 70 for use in supporting an injured musculoskeletal structure of injured finger I, including injured interphalangeal joints and/or injured metacarpophalangeal joints. As illustrated in FIG. 8, the support shell 60 juxtaposes the phalanges of the injured finger I to reduce injurious contact with foreign objects and undesired bending of the injured finger I. Particularly, the support shell 60 includes a tubular wall 61 having a slippery interior surface 65 and an exterior surface 66. The tubular wall 61 defines a central cavity 69 accessible from at least one open end of the support shell 60. The interface member 70 covers the injured finger I and includes a slippery external surface 75 that slides freely against the interior surface 65 of the support shell 60. The support shell 60 can be formed from any suitable material, including plastics, metals, composite materials, and other materials used for splinting and casting.

In use, and as illustrated in FIG. 8, a wearer, or a nurse, physician, or other caregiver, places the interface member 70 over the injured finger I. As discussed above with respect to the interface member 27, the interface member 70 can include a sock and/or an elastic support material, or other flexible, rigid, or semi-rigid support devices. The wearer or caregiver also places the support shell 60 juxtaposing the injured musculoskeletal structure of the injured finger I. For example, the wearer or caregiver inserts the injured finger I into the support shell 60 such that the support shell partially or fully encloses the injured finger I to protect against injury and to support the injured finger I using an attachment device 80. The wearer or caregiver secures the support shell 60 to an adjacent healthy finger H, or another adjacent healthy musculoskeletal structure of the limb, such as the hand, wrist, or forearm. The support shell 60 can be attached to a contiguous adjacent musculoskeletal structure, such as the palm, that is adjacent to the injured finger, using the attachment device 80. For example, tape, ties, straps, or the like, are used to secure the shell 60 to the healthy finger H for limiting movement of the support shell 60 relative to an adjacent healthy musculoskeletal structure of the limb. Additionally, the interior cavity of the support shell 60 is large enough to provide clearance space between the support shell 60 and the interface member 70 to allow for radial movement of the enclosed interface member 70. The space provided may be from about 0.1" to about 0.3" around the circumference of the interface member. Thus, as the healthy finger H moves, and as the support shell 60 moves with the healthy finger H, the injured finger I is mobilized to move freely within the support shell 60. For additional protection, the distal end of the injured finger I should not extend beyond the distal end of the support shell 60 when in use. The distal end of the support shell 60 can be open, closed, or partially open for ventilation.

Instead of placing the interface member 70 on the injured finger I, the interface member 70 can be attached to the support shell 60 such that the interior surface 65 is covered by the interface member 70. The interface member can be formed from an elastic tubular material such that the interface member 70 narrows within the support shell 60 to cushion the injured finger I during use. For example, the ends of the elastic tubular interface member 70 can be attached to the ends 61 and 62 of the support shell 60 such that the middle portion of the tubular elastic interface member 70 is free to slide over and move within the interior surface 65 of the support shell 60. Thus, the support shell 60 and the interface member 70 in such a configuration can mobilize the injured finger by suspending, cushioning, and sliding. Furthermore, the support shell 60 can be sized such that the injured finger I can move with minimized contact with the interior surface 65 of the support shell 60. For additional protection, the distal end of the injured finger I should not extend beyond the distal end of the support shell 60 when in use. The distal end of the support shell 60 can be open, closed, or partially open for ventilation.

Figures 9, 9A:
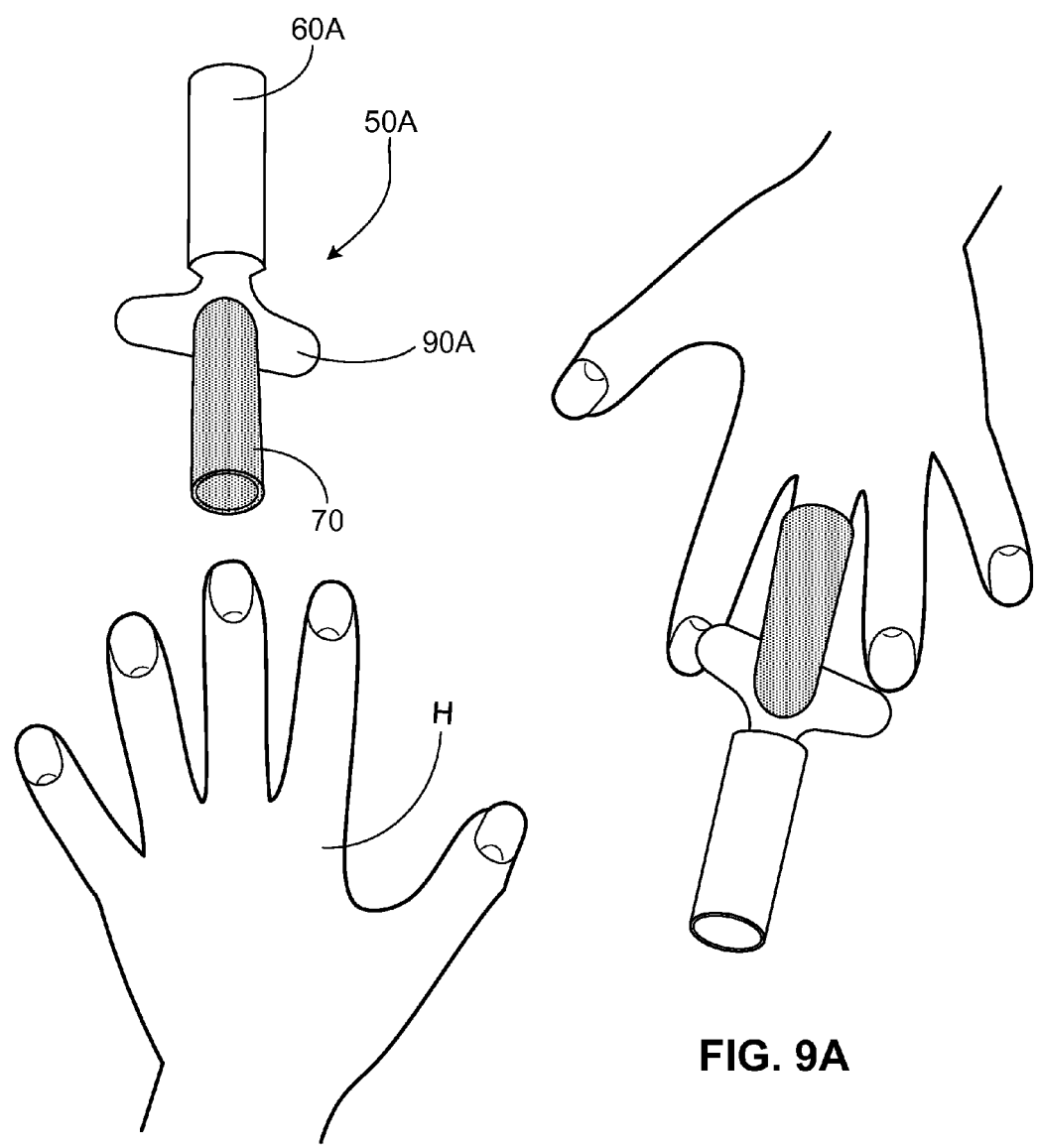
FIG. 9 is an exploded view of another orthotic support device.
FIGS. 9A and 9B are perspective views of the orthotic support device of FIG. 9.
Figure 9B:
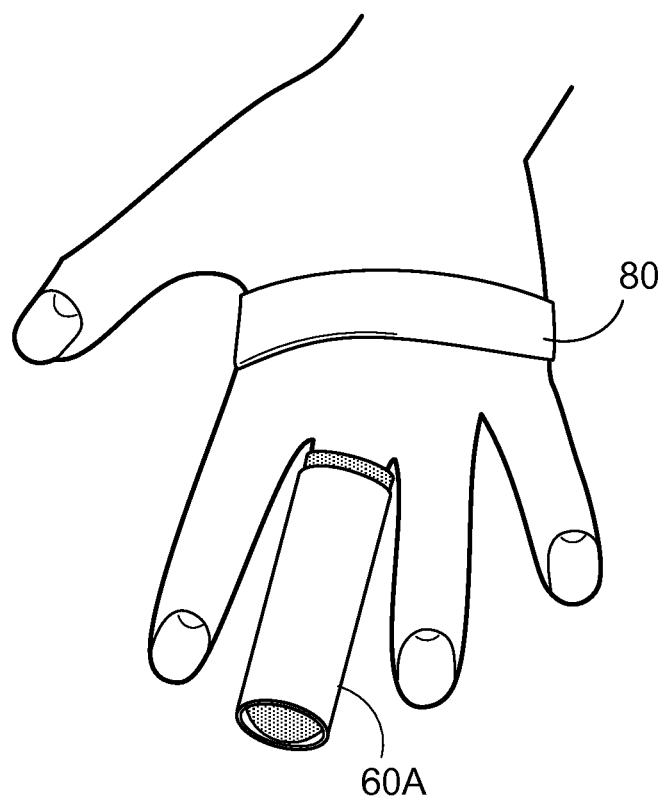

As illustrated in FIGS. 9-9B, a support device 50A includes a tab 90A included with the support shell 60A. The tab 90A provides secure attachment to the wearer's hand H using the attachment device 80. The tab 90A can be rigid or resilient to limit or inhibit bending of the injured finger I. Alternatively, the tab 90A can be flexible such that the tab 90A does not inhibit bending of the injured finger I at the metacarpophalangeal joint. Support devices with different characteristics may be indicated for different applications. For example, the tab 90A can be shaped to extend beneath one or more metacarpal heads depending on the circumstances.

Figure 10:
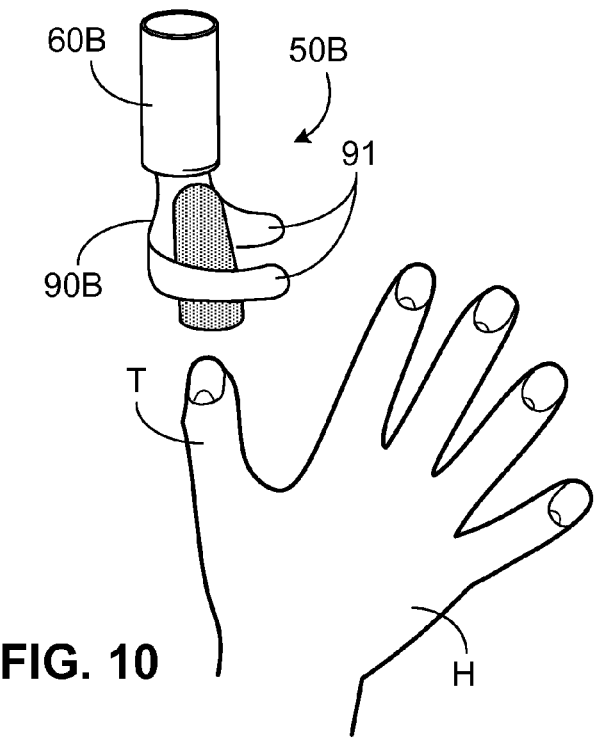
FIG. 10 is an exploded view of another orthotic support device.
Figure 10A:
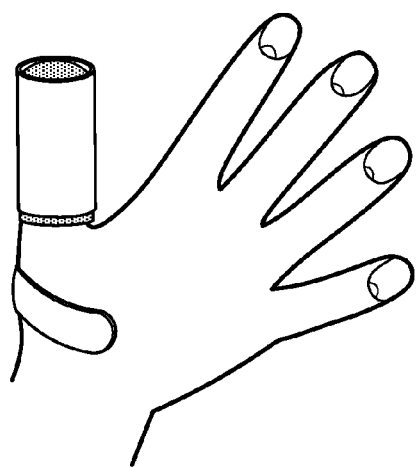
FIGS. 10A and 10B are perspective views of the orthotic support device of FIG. 10 in use.
Figure 10B:
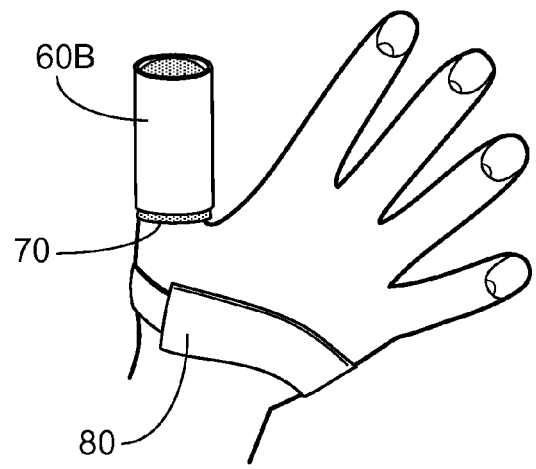

As illustrated in FIGS. 10-10B, a support device 50B supports an injured thumb T. The tab 90B is configured as a body-engaging clip with arms 91. The arms 91 are resilient and deformable to fit over the wearer's hand H. The arms 91 exert a retaining force, such as by spring action, to secure the support device 50B to the wearer's hand H, as shown in FIG. 10A. Additionally or alternatively, as shown in FIG. 10B, the support device 50B can be retained in a position juxtaposing the injured musculoskeletal structure of the thumb T using the attachment device 80 wrapped around and/or adhered to the hand H. The tab 90B can be modified or extended to provide varying engagement or attachment with the hand, wrist or arm as deemed appropriate for a particular condition.

Figure 11A:
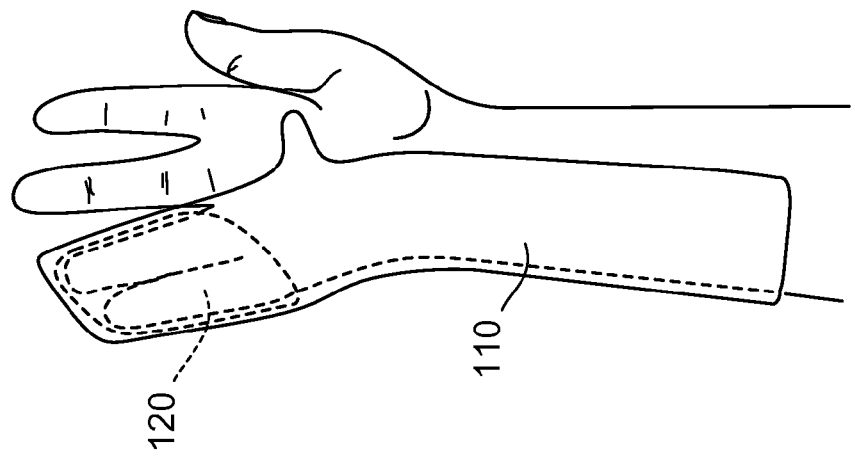
FIG. 11A is a perspective views of the orthotic support device of FIG. 11 in use.
Figure 11:
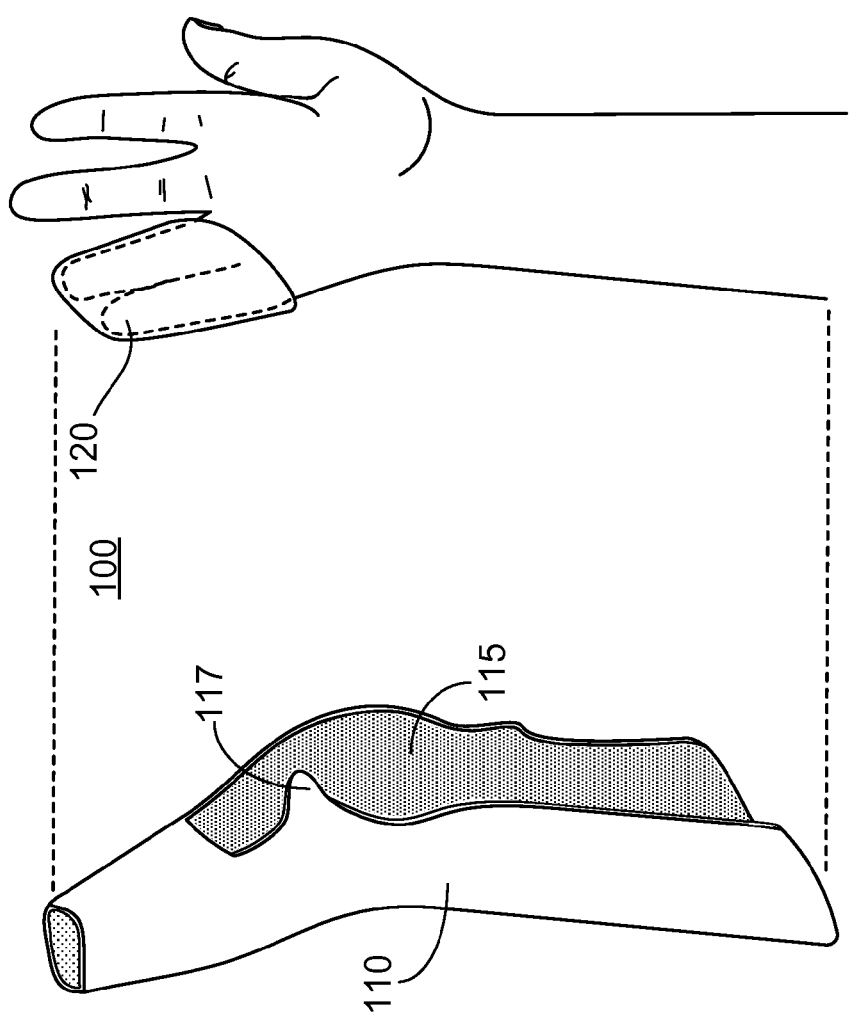
FIG. 11 is an exploded view of another orthotic support device.

Referring now to FIGS. 11 and 11A, a support device 100 includes a contoured support shell 110 that, in use and as illustrated in FIG. 11A, juxtaposes musculoskeletal structures in the wearer's arm, wrist, and hand, including fingers. The support shell 110 can be used to support, for example, a fractured metacarpal bone adjacent to the arm, wrist and hand. Thus, the support shell 110 is sufficiently rigid to protect the fracture site. The support device 100 also includes an interface member 120 for covering the finger adjoining the fractured bone, and one or more fingers adjacent thereto. The support shell 110 includes a slippery interior surface 115 to allow the interface member 120 to slide freely thereover to mobilize the fingers adjoining the fractured bone relative to the support shell 110. Thus, when the interface member 120 is placed over the finger adjoining the fracture and over the adjacent finger and when the support shell 110 is placed juxtaposing the fracture site, as illustrated in FIG. 11A, the interface member 120 mobilizes the fingers to slide freely over the slippery interior surface 115 to reduce forces applied to the fractured metacarpal bone as the fingers are flexed, or as the hand or arm pushes forward or pulls rearward in the support shell. For additional protection, the distal end of the interface member 120 does not extend beyond the distal end of the support shell 110 during use. The distal end of the support shell 110 can be open, closed, or partially open, such as including perforations or other ventilating structure.

The support shell 110 also includes a tab 117 that retains the support device 110 in position on the wearer's hand and arm. For example, the tab 117 can press inward against the wearer's hand to apply a retaining force. Alternatively, the tab 117, and/or other portions of the support shell 110 can include a tacky surface that adheres to the wearer's skin. Alternatively, the support device 100 can be secured using a strap, tape, or other attachment device.

A number of implementations have been described, and share many features. For example, the various support shell implementations described above each extends a distance beyond an anticipated range of motion of an injured musculoskeletal structure, or a musculoskeletal structure adjacent thereto, in order to reduce the opportunity for contact with foreign objects. Nevertheless, it will be understood that various modifications may be made without departing from the spirit and scope of the invention.

For example, a low friction interface can be created between a surface of any type of support or brace and the wearer's skin. As one example, a soft, elastomeric knee brace can be provided with a low friction surface facing the wearer's skin in the area of the kneecap, and can be worn with a thin liner, e.g., of fabric, that provides a low coefficient of friction interface where it contacts the low friction surface.

Moreover, in the context of the toe support device discussed above, other areas of the shoe portion 12 can be provided with a sliding surface, in addition to the footbed. For example, if the wearer has an injury to another part of the foot, or if a particular musculoskeletal condition requires additional controlled restraint of motion around the injury site, a sliding surface can be provided on the interior of the shoe upper in the area of that injury.

Additionally, injured musculoskeletal structures that can be supported and/or protected as described above include broken or bruised bones, torn or strained ligaments, torn or bruised cartilage, or torn or strained muscles. Similarly, malformed structures, and diseased structures, such as musculoskeletal structures affected by rheumatory diseases, can be supported and/or protected as described above. Moreover, while mobilization of musculoskeletal structures has been described above with respect to support and/or protection during healing of an injury, the musculoskeletal structures can be mobilized in many situations, which, for the purpose of this disclosure, are considered to be included in the term healing. For example, an injured musculoskeletal structure can be mobilized during support and/or protection thereof while more critical injuries are addressed. Additionally, in situations involving chronic diseases, pain management or other maintenance procedures are considered to be included in the term healing as used herein.

Accordingly, other embodiments are within the scope of the following claims.

What is claimed is:

1. A device for protecting an injured finger or thumb, comprising:
   a. a rigid shell member sized and shaped to juxtapose an injured finger or thumb, wherein the rigid shell member comprises a digit-facing surface portion forming an interior surface configured to enclose at least a portion of the length of the injured finger or thumb within a central cavity, wherein the digit-facing surface portion comprises a material that provides a low friction interface with the injured finger or thumb, thereby allowing the injured finger or thumb to slide freely within the central cavity; and b. an attachment device configured to secure the rigid shell member to a musculoskeletal structure adjacent to the injured finger or thumb, thereby immobilizing the rigid shell member relative to the adjacent musculoskeletal structure, wherein the attachment device comprises at least one of a tape, a strap, a tie, and a clip.

2. The device of claim 1, wherein the rigid shell member defines an opening for ventilation.

3. The device of claim 1, further comprising a tab, wherein the tab is rigid, resilient or flexible.

4. The device of claim 1 wherein the rigid shell member is in the shape of a tube.

5. The device of claim 1, further comprising an interface member positioned between the digit-facing surface portion and at least a portion of the injured finger or thumb.

6. The device of claim 5, wherein the interface member comprises an elastic material.

7. The device of claim 5, wherein the interface member comprises a flexible, rigid or semi-rigid support material.

8. The device of claim 5, wherein the interior surface is configured to provide a clearance space of about 0.1 inch to about 0.3 inches around the circumference of the interface member.

9. The device of claim 1 wherein the rigid shell member is sized and shaped to provide clearance space between the rigid shell member and the injured finger or thumb such that a transfer of force between the shell member and the injured finger or thumb is limited.

10. The device of claim 1 wherein the musculoskeletal structure is a digit adjacent to the injured finger or thumb.

11. The device of claim 1, wherein the musculoskeletal structure is a wrist adjacent to the injured finger or thumb.

12. A support device for protecting a musculoskeletal injury site involving a finger or thumb, comprising:

a) a support shell comprising a rigid wall defining a cavity for receiving at least a part of an injured finger or thumb, the rigid wall having an interior surface that extends along a length of the injured finger or thumb, the interior surface facing multiple phalanges of the injured finger or thumb, the support shell sized and shaped to provide clearance space, when in use, between the injured finger or thumb and the interior surface, the interior surface configured to provide a low friction interface between the interior surface and the injured finger or thumb, wherein the clearance space and the low friction interface are configured to mobilize the injured finger or thumb such that the injured finger or thumb can move freely within the cavity of the support shell; and b) an attachment device for securing the support device to an adjacent musculoskeletal structure of a wearer's hand or arm.

13. The support device of claim 12, wherein the support shell is in the shape of a tube.

14. The support device of claim 12, wherein the attachment device comprises at least one of a tape, a strap, a tie and a clip.

15. The support device of claim 12, further comprising a tab, wherein the tab is rigid, resilient or flexible.

16. The support device of claim 12, wherein the support shell defines an opening for ventilation.

17. The support device of claim 12, wherein the adjacent musculoskeletal structure is a digit adjacent to the injured finger or thumb.

18. The support device of claim 12, wherein the adjacent musculoskeletal structure is a wrist of the wearer's arm.

19. The support device of claim 12, further comprising an interface member positioned between the first digit-facing surface portion and at least a portion of the injured finger or thumb.

20. The support device of claim 19, wherein the interface member comprises an elastic material.

21. The support device of claim 19, wherein the interface member comprises a flexible, rigid or semi-rigid support material.

* * * * *